(12) United States Patent
Onishi et al.

(10) Patent No.: US 10,646,533 B2
(45) Date of Patent: May 12, 2020

(54) ABSORPTION ENHANCER FOR POLYPHENOL

(71) Applicant: Kao Corporation, Chuo-ku, Tokyo (JP)

(72) Inventors: Shintaro Onishi, Utsunomiya (JP); Shunsuke Ishii, Tokyo (JP); Kojiro Hashizume, Utsunomiya (JP)

(73) Assignee: Kao Corporation, Tokyo (JP)

( * ) Notice: Subject to any disclaimer, the term of this patent is extended or adjusted under 35 U.S.C. 154(b) by 48 days.

(21) Appl. No.: 15/780,027

(22) PCT Filed: Nov. 11, 2016

(86) PCT No.: PCT/JP2016/083498
§ 371 (c)(1),
(2) Date: May 30, 2018

(87) PCT Pub. No.: WO2017/104323
PCT Pub. Date: Jun. 22, 2017

(65) Prior Publication Data
US 2018/0369313 A1  Dec. 27, 2018

(30) Foreign Application Priority Data
Dec. 15, 2015  (JP) ................................ 2015-244659

(51) Int. Cl.
*A61K 36/00* (2006.01)
*A61K 36/82* (2006.01)
(Continued)

(52) U.S. Cl.
CPC ............ *A61K 36/82* (2013.01); *A23L 33/105* (2016.08); *A61K 31/216* (2013.01); *A61K 31/353* (2013.01); *A61K 36/21* (2013.01); *A61K 36/23* (2013.01); *A61K 36/233* (2013.01); *A61K 36/48* (2013.01); *A61P 3/10* (2018.01); *A61P 35/00* (2018.01); *A23V 2002/00* (2013.01); *A23V 2250/2132* (2013.01)

(58) Field of Classification Search
CPC ....................................................... A61K 36/00
See application file for complete search history.

(56) References Cited

U.S. PATENT DOCUMENTS

2012/0183614 A1* 7/2012 Yanae ..................... A23F 3/163
424/479

FOREIGN PATENT DOCUMENTS

EP  2 486 808 A1  8/2012
JP  2000-319154 A  11/2000
(Continued)

OTHER PUBLICATIONS

International Search Report (ISR) for PCT/JP2016/083498; I.A. fd Nov. 11, 2016, dated Dec. 20, 2016 from the Japan Patent Office, Tokyo, Japan.
(Continued)

*Primary Examiner* — Rosanne Kosson
(74) *Attorney, Agent, or Firm* — Sterne, Kessler, Goldstein & Fox P.L.L.C.

(57) ABSTRACT

An absorption enhancer for polyphenol containing at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, as an active ingredient.

13 Claims, 2 Drawing Sheets (51) Int. Cl.
  *A61K 31/216* (2006.01)
  *A61K 31/353* (2006.01)
  *A61K 36/21* (2006.01)
  *A61K 36/233* (2006.01)
  *A61K 36/48* (2006.01)
  *A23L 33/105* (2016.01)
  *A61K 36/23* (2006.01)
  *A61P 35/00* (2006.01)
  *A61P 3/10* (2006.01)

(56) References Cited

FOREIGN PATENT DOCUMENTS

| | | | |
|---|---|---|---|
| JP | 2001-302526 | A | 10/2001 |
| JP | 2001-328943 | A | 11/2001 |
| JP | 2002-241299 | A | 8/2002 |
| JP | 2002-257828 | A | 9/2002 |
| JP | 2009-247282 | A | 10/2009 |
| JP | 2011-079770 | A | 4/2011 |
| JP | 2014-034552 | A | 2/2014 |
| JP | 2014-091699 | A | 5/2014 |
| KR | 2009 0025638 | A | 3/2009 |

OTHER PUBLICATIONS

International Preliminary Report on Patentability (IPRP), Chapter I of the Patent Cooperation Treaty, including the Written Opinion for PCT/JP2016/083498; I.A. fd Nov. 11, 2016, dated Jun. 19, 2018, by the International Bureau of WIPO, Geneva, Switzerland.

Xie, Y. et al., "Milk enhances intestinal absorption of green tea catechins in in vitro digestion/Caco-2 cells model," Food Research International 53(2):793-800, Oct. 2013, Canadian Institute of Food Science and Technology, Elsevier Applied Science, Ottawa, Canada.

Nakagawa, K. et al., "Dose-dependent incorporation of tea catechins, (-)-epigallocatechin-3-gallate and (-)-epigallocatechin, into human plasma," Biosci. Biotechnol. Biochem. Dec. 1997; 61(12):1981-5, Taylor & Francis, Abingdon, Oxfordshire, UK.

Chen, L. et al., "Absorption, distribution, elimination of tea polyphenols in rats," Drug Metab Dispos. Sep. 1997;25(9):1045-50, Am. Soc. For Pharmacol. and Exp. Therap., Bethesda, MD.

Partial supplementary European search report, for EP Application No. 16 87 5307, dated Sep. 24, 2019, European Patent Office, Munich, Germany.

* cited by examiner

ABSORPTION ENHANCER FOR POLYPHENOL

TECHNICAL FIELD

The present invention relates to an absorption enhancer for polyphenol.

BACKGROUND ART

Polyphenol is one kind of plant component having a plurality of phenolic hydroxy groups in a molecule. Polyphenol is contained in almost all plants, and the number thereof reaches 5,000 species or more. Polyphenol is known as an antioxidative component that is produced by the plant for protecting its own self from active oxygen.

Green tea which is a beverage enjoyed for a long time contains a large amount of polyphenols, which are generically referred to as tea catechins, having a 3-hydroxyflavan structure. The tea catechins are known to have a great number of action useful for health, such as antioxidative action, sterilizing action, anticancer action, antitumor action, hypotensive action, blood sugar level elevation inhibitory action, body fat-reducing action and anti-fatigue action.

Moreover, a chlorogenic acid compound (chlorogenic acids) that is first isolated from coffee beans and is an ester compound of cinnamic acid or a derivative thereof and quinic acid is also one kind of polyphenol. This chlorogenic acid compound is known to have action of inhibiting elevation of a postprandial blood sugar level, or the like.

However, it is known that, even if polyphenol such as the tea catechins and the chlorogenic acid compound is orally ingested, absorptivity into a living body is low. For example, when a human or a rat orally ingests epigallocatechin gallate that is one kind of tea catechins and a water-soluble low-molecular weight substance, a migration rate thereof into blood is as significantly low as about 2% (for example, see Non-Patent Literatures 1 and 2).

Therefore, a great number of researches for improving absorption of polyphenol such as catechins and the chlorogenic acid compound into the living body have been conducted. For example, Patent literatures 1 and 2 describe an absorption enhancer for a catechin compound, containing serine, aspartic acid, malic acid, capric acid, lauric acid, grapefruit juice, succinic acid, cysteine, asparagine, isoleucine, pinitol, or the like, as an active ingredient.

CITATION LIST

Patent Literatures

Patent Literature 1: JP-A-2009-247282 ("JP-A" means unexamined published Japanese patent application)
Patent Literature 2: JP-A-2011-79770

Non-Patent Literatures

Non-Patent Literature 1: K. NAKAGAWA, et al., Biosci. Biotech. Biochem., 1997, vol. 61(12), p. 1981-1985
Non-Patent Literature 2: L. Chen, et al., Drug Metab. Dispos., 1997, vol. 25(9), p. 1045-1050

SUMMARY OF INVENTION

The present invention relates to an absorption enhancer for polyphenol or a food or drink composition for enhancing absorption of polyphenol, containing at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, as an active ingredient.

Further, the present invention relates to a method of producing a medical composition or a food or drink composition, containing formulating a medical composition or a food or drink composition containing polyphenol with the above-described absorption enhancer for polyphenol.

BRIEF DESCRIPTION OF THE DRAWINGS

{FIG. 1}

{FIG. 2}

{FIG. 3}

{FIG. 4}

DETAILED DESCRIPTION OF THE INVENTION

Mode for Carrying Out the Invention

The present invention relates to an absorption enhancer for polyphenol or a food or drink composition for enhancing the absorption of polyphenol, which is capable of enhancing the absorption of polyphenol into a living body.

Moreover, the present invention relates to a method of producing a medical composition or a food or drink composition, in which the medical composition or the food or drink composition are produced by taking advantage of efficacy of the above-described absorption enhancer for polyphenol as a means of administration thereof.

The present inventors diligently conducted study about a new material capable of enhancing the absorption of polyphenol into a living body. As a result, the present inventors found that above-described plant extracts have a function to enhance the absorption of polyphenol. The present invention was completed based on these findings.

The absorption enhancer for polyphenol or the food or drink composition for enhancing the absorption of polyphenol can enhance the absorption of polyphenol into the living body effectively.

Moreover, according to the method of producing the medical composition or the food or drink composition of the present invention, the medical composition or the food or drink composition excellent in the absorption of polyphenol into the living body can be produced by taking advantage of the efficacy of the above-described absorption enhancer for polyphenol.

Other and further features and advantages of the invention will appear more fully from the following description, appropriately referring to the accompanying drawings.

The term "prevention" as used herein means the prevention or delay of the onset of disease or symptom in individual bodies, or reduction in the risk of the onset of disease or symptom in individual bodies.

Further, the term "amelioration" as used herein means an improvement or alleviation of disease, symptom or condition, prevention or delay of aggravation of disease, symptom or condition, or reverse, prevention or delay of the progress of disease, symptom or condition.

Further, the term "non-therapeutic" as used herein is a concept excluding a medical action, that is, treatment action on human bodies by therapy.

The present invention provides an invention in which an application of the above-mentioned plant extracts are limited in order to enhance absorption of polyphenol into the living body. Particularly, an absorption enhancer for polyphenol of the present invention contains at least one kind of extracts selected from the group consisting of an extract of *Kochia scoparia* (L.) Schrad., an extract of *Acacia concinna*, an extract of *Sanicula europaea*, an extract of *Bupleurum rotundifolium*, and a seed extract of *Camellia sinensis*, as an active ingredient. Further, the present invention of a food or drink composition for enhancing the absorption of polyphenol contains at least one kind of extracts selected from the group consisting of an extract of *Kochia scoparia* (L.) Schrad., an extract of *Acacia concinna*, an extract of *Sanicula europaea*, an extract of *Bupleurum rotundifolium*, and a seed extract of *Camellia sinensis*, as an active ingredient.

The term "absorption enhancement for polyphenol" herein means enhancing absorption of polyphenol into the living body, particularly, from an intestinal tract into blood.

Moreover, the term "polyphenol" herein means compounds including a compound that is a polyoxy derivative of 3-oxyflavan and represented by a molecular formula "$C_{15}H_{14}O_6$" and a series of catechins corresponding to the derivative thereof, and a chlorogenic acid compound. The absorption enhancer for polyphenol, and the food or drink composition for enhancing the absorption of polyphenol of the present invention can be preferably used for absorption of tea catechins extracted from tea leaves or chlorogenic acid compounds contained in coffee beans or fruits or leaves of dicotyledons into the living body. Specific examples of the polyphenol include free catechins such as epigallocatechin (hereinafter, also referred to as "EGC"), epicatechin (hereinafter, also referred to as "EC"), catechin (hereinafter, also referred to as "C"), and gallocatechin (hereinafter, also referred to as "GC"); gallate-type catechins, in which a gallate group binds to the free catechins, such as epigallocatechin gallate (hereinafter, also referred to as "EGCg"), epicatechin gallate (hereinafter, also referred to as "ECg"), catechin gallate (hereinafter, also referred to as "Cg"), and gallocatechin gallate (hereinafter, also referred to as "GCg"); and chlorogenic acid compounds such as caffeoylquinic acid (3-caffeoylquinic acid, 4-caffeoylquinic acid, 5-caffeoylquinic acid (chlorogenic acid), or the like), feruloylqunic acid (3-feruloylquinic acid, 4-feruloylquinic acid, 5-feruloylqunic acid or the like), and dicaffeoylquinic acid (3,4-dicaffeoylquinic acid, 3,5-dicaffeoylquinic acid, 4,5-dicaffeoylquinic acid, or the like). The absorption enhancer for polyphenol or the food or drink composition for enhancing the absorption of polyphenol of the present invention preferably can be used for absorption of gallate-type catechins, especially EGCg or ECg, or chlorogenic acid compounds, especially chlorogenic acid, into the living body.

The *Kochia scoparia* (L.) Schrad. used in the present invention is an annual plant which belongs to the family Amaranthaceae, genus *Bessia*.

The *Acacia concinna* used in the present invention is an evergreen tree which belongs to the family Fabaceae syn. Leguminosae, subfamily Mimosoideae, genus *Acacieae*.

The *Sanicula europaea* used in the present invention is perennial plant which belongs to the family Apiaceae, genus *Sanicula*.

The *Bupleurum rotundifolium* used in the present invention is an annual plant which belongs to the family Apiaceae, genus *Bupleurum*.

The *Camellia sinensis* used in the present invention is an evergreen tree which belongs to the family Theaceae, genus *Camellia*.

In the preparation of the extracts from the above-described plants used as an active ingredient in the present invention, an arbitrary part of the above-described plants can be used. For example, a root, a tuberous root, a rhizome, a stock, a branch, a stem, a leaf (a leaf blade, a petiole or the like), a bark, a sap, a resin, a flower (a petal, an ovary or the like), a fruit (a ripe fruit, an unripe fruit or the like), fruit peel, a seed or the like can be used therefor. A plurality of these parts may be used in combination thereof.

Above all, the extract from *Kochia scoparia* (L.) Schrad. to be used in the present invention is preferably an extract from the fruit of *Kochia scoparia* (L.) Schrad.

Further, the extract from *Acacia concinna* to be used in the present invention is preferably an extract from the root of *Acacia concinna*.

Further, the extract from *Sanicula europaea* to be used in the present invention is preferably an extract from the leaf of *Sanicula europaea*.

Further, the extract from *Bupleurum rotundifolium* to be used in the present invention is preferably an extract from the root of *Bupleurum rotundifolium*.

Note that, in the case of using the extract from *Camellia sinensis* in the present invention, the seed of *Camellia sinensis* is used.

The plant extract to be used in the present invention can be obtained by an ordinary extraction method to be applied for extraction from a plant. The extraction method can be appropriately set up, and the extract is preferably obtained by extracting the above-described plant at room temperature or under heating, or using an extraction implement such as a Soxhlet extractor.

In preparation of the plant extract, the plant can be directly used; or dried and ground, and then used. Moreover, a steam distilled object or pressed object of the plant can also be used, and as these objects, a purified object from essential oil or the like, or a commercial item can also be used. The plant, or the steam distilled object or pressed object thereof can be used alone in any one thereof, or in combination of two or more kinds.

An extraction solvent used for preparation of the extract from the plant can be appropriately selected. Examples thereof include one ordinary used for extracting a plant, such as water; alcohols such as methanol, ethanol, propanol and butanol; polyhydric alcohols such as ethylene glycol, propylene glycol, 1,2-butylene glycol, 1,3-butylene glycol, 1,4-butylene glycol, and 2,3-butylene glycol; ketones such as acetone and methyl ethyl ketone; esters such as methyl acetate and ethyl acetate; linear or cyclic ethers such as tetrahydrofuran and diethyl ether; polyethers such as polyethylene glycol; halogenated hydrocarbons such as dichloromethane, dichloroethane, chloroform, and carbon tetrachloride; hydrocarbons such as hexane, cyclohexane and petroleum ether; aromatic hydrocarbons such as benzene and toluene; pyridines; supercritical carbon dioxide; oils and fats, waxes, and other oils. These may be used alone or in combination of two or more kinds. Above all, water, methanol, ethanol, a methanol aqueous solution, or an ethanol aqueous solution is preferred; and water, ethanol, or an ethanol aqueous solution is more preferred. Moreover, upon extraction, acid, alkali or the like may be added to adjust pH of the extraction solvent.

As extraction conditions, ordinary conditions can also be applied. For example, the plant may be subjected to immersion or heating under reflux at 0° C. or higher, preferably 4° C. or higher, and 100° C. or lower, preferably 80° C. or lower, and further preferably 40° C. or lower, for 1 minute or more, preferably 1 hour or more, and further preferably 1 day or more, and 50 days or less, preferably 30 days or less. In order to improve extraction efficiency, stirring may be simultaneously carried out or homogenization treatment may be applied in the solvent. An amount of the extraction solvent to be used is once or more, preferably 5 times or more, and 100 times or less, preferably 50 times of less, further preferably 40 times or less, based on the weight (on dried basis) of the plant.

In the present invention, the extract from the plant may be directly used. Alternatively, a fraction having higher activity obtained by further fractionating the extract by an appropriate separating technique such as gel filtration, chromatography or precision distillation can also be used. Moreover, the extract from the plant obtained therefrom is diluted, concentrated or freeze-dried, and then prepared in a powder or paste form, and the resultant material can also be used. Moreover, the extract obtained by the above-described method is subjected to solvent substitution using a solvent different from the extraction solvent, and then the resultant material can also be used.

The term "extract" in the present invention includes extracts by various kinds of solvents as obtained by the extraction methods described above, a diluted liquid thereof, a concentrated liquid thereof, a purified fraction thereof, dried powder thereof, or a liquid thereof subjected to solvent substitution.

In the absorption enhancer for polyphenol or the food or drink composition for enhancing the absorption of polyphenol of the present invention, the above-described active ingredient may be used alone in one kind or in combination of two or more kinds thereof.

As demonstrated in Examples mentioned later, the above-mentioned active ingredient has action of enhancing permeation of polyphenol from a lumen side to a basement membrane side in an in vitro model using a monolayer culture cell of a Caco-2 cell being an epithelial cell line derived from a human colon carcimoma. This in vitro model has been already verified to have a correlation with permeation absorption in a human intestinal tract in vitro. Accordingly, the above-described active ingredient having action of enhancing permeation of polyphenol in the above-described in vitro model is also effective in enhancing the absorption of polyphenol into the living body, particularly, from the intestinal tract into blood also in vivo.

The above-described active ingredient may be used as an absorption enhancer for polyphenol. Further, the above-described active ingredient may be used for producing the absorption enhancer for polyphenol.

A form of the absorption enhancer for polyphenol of the present invention can be appropriately selected. For example, the above-described active ingredient itself may be used as the absorption enhancer for polyphenol of the present invention. Alternatively, the absorption enhancer for polyphenol containing the above-described active ingredient and a pharmaceutically acceptable carrier, according to the present invention may be used as the medical composition. Alternatively, the above-described active ingredient itself or the absorption enhancer for polyphenol of the present invention may be incorporated into a food or drink composition.

Here, the absorption enhancer for polyphenol of the present invention includes an aspect in which the above-described extract itself is applied as the active ingredient. Further, the absorption enhancer for polyphenol of the present invention also includes an aspect of a composition containing the above-described extract as the active ingredient and containing the pharmaceutically acceptable carrier or various additives.

Hereinafter, the aspect of the composition containing the above-described extract as the active ingredient and containing the pharmaceutically acceptable carrier or various additives will be described.

When the medical composition is prepared as an absorption enhancer for polyphenol of the present invention, the composition is ordinarily prepared as a preparation containing the above-described active ingredient and preferably a pharmaceutically acceptable carrier. The pharmaceutically acceptable carrier generally means an inert, nontoxic, solid or liquid extender, diluent, encapsulation material or the like that does not react with the above-described active ingredient, and specific examples include a solvent or a dispersion medium such as water, ethanol, polyols, a suitable mixture thereof and vegetable oil.

The medical composition is orally or parenterally administered into, for example, an oral cavity, a digestive organ, or a nasal cavity. Specific examples of orally administrable preparations include a tablet, a granule, a fine granule, powder, a capsule, a chewable agent, a pellet, a syrup, a liquid, a suspension and an inhalation. Specific examples of parenterally administrable preparations include a drop, a nasal drop, and an injection.

The medical composition may further contain a conventional additive in a medicine field. Examples of such an additive include an excipient, a binder, a disintegrator, a lubricant, an antioxidant, a colorant and a corrigent. The additive can be used when necessary. In order to achieve sustained release such that the composition can be effected for a long time, the composition can also be coated with a known retardant or the like. Other additives or chemicals may be added thereto, when necessary, for example, an antacid or a gastric mucosa protective agent may be added thereto.

The above-described medical composition can be applied in the form of a stomatological composition, an internal application composition or the like. Moreover, the above-described medical composition may be used for therapy or non-therapy.

The absorption enhancer for polyphenol of the present invention can be used by being added to food, drink, feed, or pet food, or being mixed with them. Alternatively, the absorption enhancer for polyphenol of the present invention can be used as drink or food, by itself. Alternatively, the absorption enhancer for polyphenol of the present invention can be used by being added or blended into food or drink indicating the concept of the enhancement of polyphenol absorption, that is, into a health food, a food with function claims, a food for sick people, or a food for specified health uses. Moreover, the absorption enhancer for polyphenol of the present invention can be used by being added or blended into food and drink, which contains polyphenol and indicates the concept of treatment or prevention, or treatment, prevention, improvement or the like of a disease or condition that can be treated by polyphenol, that is, into a health food, a food with function claims, a food for sick people, or a food for specified health uses. The above-described health food, food with function claims, food for sick people, or food for specified health uses can be used, specifically, in the form of various kinds of preparations such as a fine granule, a tablet, a granule, powder, a capsule, a syrup, a liquid and a liquid diet. The food in the form of the preparation can be manufactured, in a manner similar to a medical preparation, by mixing the above-described active ingredient and a carrier acceptable as the food, and for example, a suitable excipient and so forth, and applying a conventional means. Further, the food or drink composition can be manufactured by being added or blended the absorption enhancer for polyphenol of the present invention into a liquid drink composition such as soups, juices, a fruit juice drink, milk, a milk beverage, a whey beverage, a lactic acid bacteria beverage, a tea beverage, an alcoholic beverage, a coffee beverage, soda, a refreshing beverage, a drinking water, a cocoa beverage, a jelly-like beverage, a sport drink and a diet beverage; a semi-solid food composition such as pudding and yogurt; noodles; confectionaries; and spreads.

The food or drink composition may be blended with various kinds of food additives alone or in combination thereof, for example, additives which is used as materials of ordinarily food or drink, such as an antioxidant, a colorant, a spice, a condiment, a sweetener, an acidulant, a pH adjuster, a quality stabilizer and a preservative.

The food or drink composition can be filled into an ordinary packaging container such as a molded container containing polyethylene terephthalate as a main component (PET bottle), a metal can, a paper container combined with metallic foil or plastics film, and a bottle, and provided.

Moreover, the food or drink composition can be manufactured under sterilization conditions specified in laws and regulations (Food Sanitation Act in Japan) to be applied, for example, when the composition is filled into the container such as the metal can, and then the whole can be sterilized by heat. For a material enabling no retort sterilization, such as the PET bottle or the paper container, such a method can be adopted in which the material is sterilized under sterilization conditions equivalent to the above-described conditions in advance, for example, at a high temperature for a short period of time by a plate-type heat exchanger or the like, and then cooled to a predetermined temperature, and then the composition is filled into the container.

The content of the above-described active ingredient in the composition containing the absorption enhancer for polyphenol or food or drink composition for enhancing the absorption of polyphenol of the present invention can be appropriately determined.

For example, in the total amount of the compositions containing the active ingredient, the content of the active ingredient is preferably 0.01 mass % or more, and more preferably 1 mass % or more. The upper limit thereof is preferably 99.9 mass % or less, more preferably 80 mass % or less, further preferably 50 mass % or less, and furthermore preferably 10 mass % or less. Further, the numerical range of the content of the active ingredient is preferably 0.01 to 99.9 mass %, more preferably 0.01 to 80 mass %, further preferably 1 to 50 mass %, and furthermore preferably 1 to 10 mass %.

An administration or ingestion object of the absorption enhancer for polyphenol or the food or drink composition for enhancing the absorption of polyphenol of the present invention is preferably a warm-blooded vertebrate, and more preferably a mammal. Specific examples of the mammals herein include a human and a non-human mammal such as a monkey, a mouse, a rat, a rabbit, a dog, a cat, a bovine, a horse and a pig. The absorption enhancer for polyphenol or the food or drink composition for enhancing the absorption of polyphenol of the present invention is preferably administered or ingested to a human.

The absorption enhancer for polyphenol or the food or drink composition for enhancing the absorption of polyphenol of the present invention can be preferably applied to a subject who desires enhancement of polyphenol absorption. Alternatively, the absorption enhancer for polyphenol or the food or drink composition for enhancing the absorption of polyphenol of the present invention can also be preferably applied to a person who desires an antiaging effect, a life-extension effect, a cognitive function maintaining effect, an antioxidative effect, a sterilizing effect, a preventive effect on an infectious disease, a relieving effect of an infectious disease symptom, an anticancer effect, an antitumor effect, a hypotensive effect, a blood sugar level elevation inhibitory effect, a body fat-reducing effect, an anti-fatigue effect or improvement of stamina, a person who desires reduction of body fat, a person of lack of exercise, middle-aged and senior persons, a patient of diabetes mellitus or insulin resistance, a subject who is not suffered from diabetes mellitus or insulin resistance, and has high postprandial blood sugar but has no abnormality in fasting blood sugar, a subject who does not need to decrease the fasting blood sugar but desires to reduce the high postprandial blood sugar, and also those who are likely to develop the above-described symptoms.

Moreover, the absorption enhancer for polyphenol or the food or drink composition for enhancing the absorption of polyphenol of the present invention can be preferably applied under conditions in which the absorption of polyphenol into the living body, preferably, from the intestinal tract into blood is suppressed. Further, the absorption enhancer for polyphenol or the food or drink composition for enhancing the absorption of polyphenol of the present invention is preferably orally administered.

The absorption of polyphenol into the living body can be enhanced by administrating or ingesting the above-described active ingredient and polyphenol into a human or a nonhuman animal.

Thus, in the method of enhancing the absorption of polyphenol into the living body by using the absorption enhancer for polyphenol or the food or drink composition for enhancing the absorption of polyphenol of the present invention, an effective dose of the above-described active ingredient to be applied by administrating or ingesting the composition can be appropriately determined according to a state of an individual, a body weight thereof, a sex thereof, an age thereof, activity of a raw material, a pathway of administration or ingestion, a schedule of administration or ingestion, a preparation form or other factors. For example, the amount of administration or ingestion of the active ingredient is preferably 0.001 mg/kg body weight/day or more, more preferably 0.01 mg/kg body weight/day or more, and further preferably 0.5 mg/kg body weight/day or more. The upper limit thereof is preferably 50 mg/kg body weight/day or less, and more preferably 10 mg/kg body weight/day or less. Further, the numerical range of the amount of administration or ingestion of the active ingredient is preferably 0.001 to 50 mg/kg body weight/day, more preferably 0.01 to 50 mg/kg body weight/day, further preferably 0.01 to 10 mg/kg body weight/day, and furthermore preferably 0.5 to 10 mg/kg body weight/day.

The amount of administration or ingestion of the active ingredient is preferably 0.01 or more parts by mass, more preferably 0.1 or more parts by mass, and further preferably 5 or more parts by mass, relative to 100 parts by mass of polyphenol. The upper limit thereof is preferably 500 or less parts by mass, and more preferably 100 or less parts by mass, relative to 100 parts by mass of polyphenol. Further, the numerical range of the amount of administration or ingestion of the active ingredient is preferably 0.01 to 500 parts by mass, more preferably 0.1 to 500 parts by mass, further preferably 0.1 to 100 parts by mass, and furthermore preferably 5 to 100 parts by mass, relative to 100 parts by mass of polyphenol.

The absorption enhancer for polyphenol or the food or drink composition for enhancing the absorption of polyphenol of the present invention can be ingested or administered once a day or divisionally several times a day or during an arbitrary period or at intervals. In the present invention, the absorption enhancer for polyphenol or the food or drink composition for enhancing the absorption of polyphenol of the present invention and polyphenol may be simultaneously administered or ingested, or need not be simultaneously administered or ingested. Especially, the absorption enhancer for polyphenol or the food or drink composition for enhancing the absorption of polyphenol of the present invention and polyphenol is preferably simultaneously administered or ingested.

The expression "simultaneously administered or ingested" herein means that the absorption enhancer for polyphenol or the food or drink composition for enhancing the absorption of polyphenol of the present invention and polyphenol are simultaneously administered or ingested in terms of time, and also that the absorption enhancer for polyphenol or the food or drink composition for enhancing the absorption of polyphenol of the present invention and polyphenol are separately administered or ingested in terms of time, but timing at which the absorption enhancer for polyphenol or the food or drink composition for enhancing the absorption of polyphenol of the present invention and polyphenol are administered or ingested, respectively, is appropriately adjusted in such a manner that the absorption enhancer for polyphenol or the food or drink composition for enhancing the absorption of polyphenol of the present invention and polyphenol are almost simultaneously reach the intestinal tract together.

In addition, as described above, the timing of administration or ingestion of the absorption enhancer for polyphenol or the food or drink composition for enhancing the absorption of polyphenol of the present invention for allowing polyphenol and the absorption enhancer for polyphenol or the food or drink composition for enhancing the absorption of polyphenol to almost simultaneously reach the intestinal tract is preferably within 2 hours before and after administration or ingestion of polyphenol, more preferably within 1 hour before and after administration or ingestion thereof, further preferably within 30 minutes before and after administration or ingestion thereof, and still further preferably simultaneous administration or ingestion thereof in terms of time.

By blending the medical composition or the food or drink composition containing polyphenol with the above-described active ingredient, the medical composition or the food or drink composition excellent in absorption of polyphenol into the living body can be manufactured by taking advantage of the efficacy of the absorption enhancer for polyphenol or the food or drink composition for enhancing the absorption of polyphenol of the present invention.

Blending of polyphenol or the medical composition containing polyphenol with the above-described active ingredient can be performed by an ordinary method. For example, polyphenol or a composition containing the polyphenol can be mixed with the absorption enhancer for polyphenol or food or drink composition for enhancing absorption of polyphenol of the present invention according to an ordinary method. Alternatively, polyphenol or a composition containing polyphenol can be added to the absorption enhancer for polyphenol or food or drink composition for enhancing absorption of polyphenol of the present invention. Herein, the combination ratio of polyphenol with the above-described active ingredient to be used in the absorption enhancer for polyphenol or food or drink composition for enhancing absorption of polyphenol is preferably 10,000:1 or more, more preferably 1,000:1 or more, further preferably 100:1 or more, or furthermore preferably 10:1 or more, by weight. The upper limit thereof is preferably 1:5 or less, or more preferably 1:1 or less. Further, the numerical range thereof is preferably 10,000:1 to 1:5, more preferably 1,000:1 to 1:5, further preferably 100:1 to 1:5, furthermore preferably 10:1 to 1:5, or furthermore preferably 10:1 to 1:1.

With regard to the embodiments described above, the present invention also discloses an absorption enhancer for polyphenol, a food or drink composition, a plant extract, a method of using thereof, a composition containing thereof, and a method of producing thereof, described below.

<1> An absorption enhancer for polyphenol containing at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, as an active ingredient.

<2> A food or drink composition for enhancing the absorption of polyphenol containing at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, as an active ingredient.

<3> The absorption enhancer for polyphenol or the food or drink composition for enhancing the absorption of polyphenol described in the above item <1> or <2>, wherein the polyphenol is preferably tea catechins, more preferably gallate-type catechins, more preferably EGCg or ECg.

<4> The absorption enhancer for polyphenol or the food or drink composition for enhancing the absorption of polyphenol described in the above item <1> or <2>, wherein the polyphenol is a chlorogenic acid compound, preferably at least one kind of chlorogenic acid compound selected from the group consisting of caffeoylquinic acid, feruloylqunic acid and dicaffeoylquinic acid; or more preferably chlorogenic acid.

<5> The absorption enhancer for polyphenol or the food or drink composition for enhancing the absorption of polyphenol described in any one of the above items <1> to <4>, which enhances absorption of polyphenol from an intestinal tract into blood.

<6> The absorption enhancer for polyphenol or the food or drink composition for enhancing the absorption of polyphenol described in any one of the above items <1> to <5>, wherein the extract from *Kochia scoparia* (L.) Schrad. is an extract from the fruit of *Kochia scoparia* (L.) Schrad.

<7> The absorption enhancer for polyphenol or the food or drink composition for enhancing the absorption of polyphenol described in any one of the above items <1> to <5>, wherein the extract from *Acacia concinna* is an extract from the root of *Acacia concinna*.

<8> The absorption enhancer for polyphenol or the food or drink composition for enhancing the absorption of polyphenol described in any one of the above items <1> to <5>, wherein the extract from *Sanicula europaea* is an extract from the leaf of *Sanicula europaea*.

<9> The absorption enhancer for polyphenol or the food or drink composition for enhancing the absorption of polyphenol described in any one of the above items <1> to <5>, wherein the extract from *Bupleurum rotundifolium* is an extract from the root of *Bupleurum rotundifolium*.

<10> The absorption enhancer for polyphenol or the food or drink composition for enhancing the absorption of polyphenol described in any one of the above items <1> to <9>, wherein the plant extract is obtained by extracting plant using water, methanol, ethanol, a methanol aqueous solution, or an ethanol aqueous solution, as an extraction solvent.

<11> The absorption enhancer for polyphenol or the food or drink composition for enhancing the absorption of polyphenol described in any one of the above items <1> to <10>, wherein the content of the active ingredient is 0.01 mass % or more, or preferably 1 mass % or more, and 99.9 mass % or less, preferably 80 mass % or less, more preferably 50 mass % or less, or further preferably 10 mass % or less, in the total amount of the absorption enhancer for polyphenol or the food or drink composition for enhancing the absorption of polyphenol.

<12> A medical composition containing the absorption enhancer for polyphenol described in any one of the above items <1> to <11>.

<13> The medical composition described in the above item <12>, which is applied in the form of a stomatological composition or an internal application composition.

<14> A food composition containing the absorption enhancer for polyphenol described in any one of the above items <1> to <11>.

<15> A method of producing a medical composition or a food or drink composition, containing formulating polyphenol or a medical composition or a food or drink composition containing polyphenol with the absorption enhancer for polyphenol or the food or drink composition for enhancing the absorption of polyphenol described in any one of the above items <1> to <11>.

<16> The method described in the above item <15>, wherein the combination ratio of polyphenol with the above-described active ingredient to be used in the absorption enhancer for polyphenol or food or drink composition for enhancing absorption of polyphenol is preferably 10,000:1 or more, more preferably 1,000:1 or more, further preferably 100:1 or more, or furthermore preferably 10:1 or more, and preferably 1:5 or less, or more preferably 1:1 or less, by weight.

<17> Use of at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, for enhancing absorption of polyphenol.

<18> Use of at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, for producing an absorption enhancer for polyphenol.

<19> A method of using at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, as an absorption enhancer for polyphenol.

<20> A method of enhancing absorption of polyphenol, containing applying at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*.

<21> The use or method described in any one of the above items <17> to <20>, wherein the polyphenol is tea catechins, preferably gallate-type catechins, more preferably EGCg or ECg.

<22> The use or method described in any one of the above items <17> to <20>, wherein the polyphenol is a chlorogenic acid compound, preferably at least one kind of chlorogenic acid compound selected from the group consisting of caffeoylquinic acid, feruloylqunic acid and dicaffeoylquinic acid, or more preferably chlorogenic acid.

<23> The use or method described in any one of the above items <17> to <22>, wherein the plant extract enhances absorption of polyphenol from an intestinal tract into blood.

<24> The use or method described in any one of the above items <17> to <23>, wherein the extract from *Kochia scoparia* (L.) Schrad. is an extract from the fruit of *Kochia scoparia* (L.) Schrad.

<25> The use or method described in any one of the above items <17> to <23>, wherein the extract from *Acacia concinna* is an extract from the root of *Acacia concinna*.

<26> The use or method described in any one of the above items <17> to <23>, wherein the extract from *Sanicula europaea* is an extract from the leaf of *Sanicula europaea*.

<27> The use or method described in any one of the above items <17> to <23>, wherein the extract from *Bupleurum rotundifolium* is an extract from the root of *Bupleurum rotundifolium*.

<28> The use or method described in any one of the above items <17> to <27>, wherein the plant extract is obtained by extracting plant using water, methanol, ethanol, a methanol aqueous solution, or an ethanol aqueous solution, as an extraction solvent.

<29> The use or method described in any one of the above items <17> to <28>, wherein the plant extract is applied to a person who desires an antiaging effect, a life-extension effect, a cognitive function maintaining effect, an antioxidative effect, a sterilizing effect, a preventive effect on an infectious disease, a relieving effect of an infectious disease symptom, an anticancer effect, an antitumor effect, a hypotensive effect, a blood sugar level elevation inhibitory effect, a body fat-reducing effect, an anti-fatigue effect or improvement of stamina, a person who desires reduction of body fat, a person of lack of exercise, middle-aged and senior persons, a patient of diabetes mellitus or insulin resistance, a subject who is not suffered from diabetes mellitus or insulin resistance, and has high postprandial blood sugar but has no abnormality in fasting blood sugar, a subject who does not need to decrease the fasting blood sugar but desires to reduce the high postprandial blood sugar, and also those who are likely to develop the above-described symptoms.

<30> The use or method described in any one of the above items <17> to <29>, which is applied under conditions in which the absorption of polyphenol into the living body, preferably, from the intestinal tract into blood is suppressed.

<31> The use or method described in any one of the above items <17> to <30>, wherein the content of the plant extract is 0.01 mass % or more, or preferably 1 mass % or more, and 99.9 mass % or less, preferably 80 mass % or less, more preferably 50 mass % or less, or further preferably 10 mass % or less, in the total amount of the absorption enhancer for polyphenol.

<32> At least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, to be used for enhancing absorption of polyphenol.

<33> Use of at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, for manufacture of drug for enhancing absorption of polyphenol.

<34> Non-therapeutic use of at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis*, for enhancing absorption of polyphenol.

<35> The plant extract or use described in any one of the above items <32> to <34>, wherein the polyphenol is tea catechins, preferably gallate-type catechins, or more preferably EGCg or ECg.

<36> The plant extract or use described in any one of the above items <32> to <34>, wherein the polyphenol is a chlorogenic acid compound, preferably at least one kind of chlorogenic acid compound selected from the group consisting of caffeoylquinic acid, feruloylqunic acid, and dicaffeoylquinic acid, or further preferably chlorogenic acid.

<37> The plant extract or use described in any one of the above items <32> to <36>, wherein the plant extract enhances absorption of polyphenol from an intestinal tract into blood.

<38> The plant extract or use described in any one of the above items <32> to <37>, wherein the extract from *Kochia scoparia* (L.) Schrad. is an extract from the fruit of *Kochia scoparia* (L.) Schrad.

<39> The plant extract or use described in any one of the above items <32> to <37>, wherein the extract from *Acacia concinna* is an extract from the root of *Acacia concinna*.

<40> The plant extract or use described in any one of the above items <32> to <37>, wherein the extract from *Sanicula europaea* is an extract from the leaf of *Sanicula europaea*.

<41> The plant extract or use described in any one of the above items <32> to <37>, wherein the extract from *Bupleurum rotundifolium* is an extract from the root of *Bupleurum rotundifolium*.

<42> The plant extract or use described in any one of the above items <32> to <41>, wherein the plant extract is obtained by extracting plant using water, methanol, ethanol, a methanol aqueous solution, or an ethanol aqueous solution, as an extraction solvent.

<43> The plant extract or use described in any one of the above items <32> to <42>, wherein the plant extract is applied to a person who desires an antiaging effect, a life-extension effect, a cognitive function maintaining effect, an antioxidative effect, a sterilizing effect, a preventive effect on an infectious disease, a relieving effect of an infectious disease symptom, an anticancer effect, an antitumor effect, a hypotensive effect, a blood sugar level elevation inhibitory effect, a body fat-reducing effect, an anti-fatigue effect or improvement of stamina, a person who desires reduction of body fat, a person of lack of exercise, middle-aged and senior persons, a patient of diabetes mellitus or insulin resistance, a subject who is not suffered from diabetes mellitus or insulin resistance, and has high postprandial blood sugar but has no abnormality in fasting blood sugar, a subject who does not need to decrease the fasting blood sugar but desires to reduce the high postprandial blood sugar, and also those who are likely to develop the above-described symptoms.

<44> The plant extract or use described in any one of the above items <32> to <43>, which is applied under conditions in which the absorption of polyphenol into the living body, preferably, from the intestinal tract into blood is suppressed.

<45> The plant extract or use described in any one of the above items <32> to <44>, wherein the plant extract is applied in the form of a medical composition.

<46> The plant extract or use described in any one of the above items <32> to <44>, wherein the plant extract is applied in forms of food, drink or feed.

<47> The plant extract or use described in any one of the above items <32> to <46>, wherein the content of the plant extract is 0.01 mass % or more, or preferably 1 mass % or more, and 99.9 mass % or less, preferably 80 mass % or less, more preferably 50 mass % or less, or further preferably 10 mass % or less.

<48> A method of enhancing absorption of polyphenol, containing administrating or ingesting at least one kind of extract selected from the group consisting of an extract from *Kochia scoparia* (L.) Schrad., an extract from *Acacia concinna*, an extract from *Sanicula europaea*, an extract from *Bupleurum rotundifolium*, and a seed extract from *Camellia sinensis* into a human or a nonhuman animal.

<49> The method described in the above item <48>, wherein the polyphenol is tea catechins, preferably gallate-type catechins, or more preferably EGCg or ECg.

<50> The method described in the above item <48>, wherein the polyphenol is a chlorogenic acid compound, preferably at least one kind of chlorogenic acid compound selected from the group consisting of caffeoylquinic acid, feruloylqunic acid, and dicaffeoylquinic acid, or further preferably chlorogenic acid.

<51> The method described in any one of the above item <48> to <50>, wherein the plant extract enhances absorption of polyphenol from an intestinal tract into blood.

<52> The method described in any one of the above items <48> to <51>, wherein the extract from *Kochia scoparia* (L.) Schrad. is an extract from the fruit of *Kochia scoparia* (L.) Schrad.

<53> The method described in any one of the above items <48> to <51>, wherein the extract from *Acacia concinna* is an extract from the root of *Acacia concinna*.

<54> The method described in any one of the above items <48> to <51>, wherein the extract from *Sanicula europaea* is an extract from the leaf of *Sanicula europaea*.

<55> The method described in any one of the above items <48> to <51>, wherein the extract from *Bupleurum rotundifolium* is an extract from the root of *Bupleurum rotundifolium*.

<56> The method described in any one of the above items <48> to <55>, wherein the plant extract is obtained by extracting plant using water, methanol, ethanol, a methanol aqueous solution, or an ethanol aqueous solution, as an extraction solvent.

<57> The method described in any one of the above items <48> to <56>, wherein the plant extract is applied to a person who desires an antiaging effect, a life-extension effect, a cognitive function maintaining effect, an antioxidative effect, a sterilizing effect, a preventive effect on an infectious disease, a relieving effect of an infectious disease symptom, an anticancer effect, an antitumor effect, a hypotensive effect, a blood sugar level elevation inhibitory effect, a body fat-reducing effect, an antifatigue effect or improvement of stamina, a person who desires reduction of body fat, a person of lack of exercise, middle-aged and senior persons, a patient of diabetes mellitus or insulin resistance, a subject who is not suffered from diabetes mellitus or insulin resistance, and has high postprandial blood sugar but has no abnormality in fasting blood sugar, a subject who does not need to decrease the fasting blood sugar but desires to reduce the high postprandial blood sugar, and also those who are likely to develop the above-described symptoms.

<58> The method described in any one of the above items <48> to <57>, which is applied under conditions in which the absorption of polyphenol into the living body, preferably, from the intestinal tract into blood is suppressed.

<59> The method described in any one of the above items <48> to <58>, wherein the amount of administration or ingestion of the plant extract is 0.001 mg/kg body weight/day or more, preferably 0.01 mg/kg body weight/day or more, or more preferably 0.5 mg/kg body weight/day or more; and 50 mg/kg body weight/day or less, or preferably 10 mg/kg body weight/day or less.

<60> The method described in any one of the above items <48> to <59>, which is a non-therapeutic method of enhancing absorption of polyphenol.

<61> A method of enhancing absorption of polyphenol, wherein polyphenol, and the absorption enhancer for polyphenol or the food or drink composition for enhancing the absorption of polyphenol described in any one of the above items <1> to <11> are administrated or ingested into a human or a nonhuman animal, to enhance absorption of polyphenol into the living body, preferably from an intestinal tract into blood.

<62> The method described in item <61>, wherein the amount of administration or ingestion of the active ingredient is preferably 0.01 or more parts by mass, more preferably 0.1 or more parts by mass, further preferably 5 or more parts by mass, and preferably 500 or less parts by mass, more preferably 100 or less parts by mass; or preferably 0.01 to 500 parts by mass, more preferably 0.1 to 500 parts by mass, further preferably 0.1 to 100 parts by mass, and furthermore preferably 5 to 100 parts by mass, relative to 100 parts by mass of polyphenol.

<63> The method described in item <61> or <62>, wherein polyphenol and the above described absorption enhancer for polyphenol are simultaneously administered or ingested, preferably polyphenol and the above described absorption enhancer for polyphenol are simultaneously administered or ingested in terms of time, or polyphenol and the above described absorption enhancer for polyphenol each are administered or ingested so as to be almost simultaneously reached the intestinal tract together, more preferably polyphenol and the above described absorption enhancer for polyphenol are simultaneously administered or ingested in terms of time.

EXAMPLES

Hereinafter, the present invention will be described more in detail with reference to Examples, but the present invention is not limited thereto. In addition, unless otherwise specified, "%" representing a composition in the present Examples means a volume composition ratio (% (v/v)) at room temperature (25° C.).

Preparation Example 1

Preparation of Extract from *Kochia Scoparia* (L.) Schrad.

To 100 g of fruit of *Kochia scoparia* (L.) Schrad. (produced in Hebei Province, obtained from Shinwa Bussan Kaisha Ltd.), 1,000 mL of 80% ethanol aqueous solution was added, and the resultant mixture was subjected to extraction at room temperature for 10 days under conditions of being left to stand. Then, the resultant material was separated from a non-extraction portion by filtration, concentrated, and freeze-dried to obtain an ethanol extract from *Kochia scoparia* (L.) Schrad.

To the obtained ethanol extract, 500 mL of water-saturated n-BuOH and 500 mL of water were added, and liquid-liquid fractionation was applied thereto. The fraction of n-BuOH was collected, a solvent was distilled off, and then acetone was added thereto, and a soluble matter was eliminated. Thus, 0.7 g of the acetone-insoluble fraction was obtained.

The obtained insoluble fraction was dissolved in a 50% ethanol aqueous solution to be 1% (w/v) in a concentration to prepare an extract from *Kochia scoparia* (L.) Schrad.

Preparation Example 2

Preparation of Extract from *Acacia Concinna*

To 100 g of root of *Acacia concinna* (produced in North America, obtained from monteagle Herbs), 1,000 mL of 80% ethanol aqueous solution was added, and the resultant mixture was subjected to extraction at room temperature for 10 days under conditions of being left to stand. Then, the resultant material was separated from a non-extraction portion by filtration, concentrated, and freeze-dried to obtain an ethanol extract from *Acacia concinna*.

To the obtained ethanol extract, 500 mL of water-saturated n-BuOH and 500 mL of water were added, and liquid-liquid fractionation was applied thereto. The fraction of n-BuOH was collected, a solvent was distilled off, and then acetone was added thereto, and a soluble matter was eliminated. Thus, 4.8 g of the acetone-insoluble fraction was obtained.

The obtained insoluble fraction was dissolved in a 50% ethanol aqueous solution to be 1% (w/v) in a concentration to prepare an extract from *Acacia concinna*.

Preparation Example 3

Preparation of Extract from *Sanicula Europaea*

To 100 g of leaf of *Sanicula europaea* (produced in North America, obtained from monteagle Herbs), 1,000 mL of 80% ethanol aqueous solution was added, and the resultant mixture was subjected to extraction at room temperature for 10 days under conditions of being left to stand. Then, the resultant material was separated from a non-extraction portion by filtration, concentrated, and freeze-dried to obtain an ethanol extract from *Sanicula europaea*.

To the obtained ethanol extract, 500 mL of water-saturated n-BuOH and 500 mL of water were added, and liquid-liquid fractionation was applied thereto. The fraction of n-BuOH was collected, a solvent was distilled off, and then acetone was added thereto, and a soluble matter was eliminated. Thus, 3.08 g of the acetone-insoluble fraction was obtained.

The obtained insoluble fraction was dissolved in a 50% ethanol aqueous solution to be 1% (w/v) in a concentration to prepare an extract from *Sanicula europaea*.

Preparation Example 4

Preparation of Extract from *Bupleurum Rotundifolium*

To 100 g of root of *Bupleurum rotundifolium* (produced in North America, obtained from monteagle Herbs), 1,000 mL of 80% ethanol aqueous solution was added, and the resultant mixture was subjected to extraction at room temperature for 10 days under conditions of being left to stand. Then, the resultant material was separated from a non-extraction portion by filtration, concentrated, and freeze-dried to obtain an ethanol extract from *Bupleurum rotundifolium*.

To the obtained ethanol extract, 500 mL of water-saturated n-BuOH and 500 mL of water were added, and liquid-liquid fractionation was applied thereto. The fraction of n-BuOH was collected, a solvent was distilled off, and then acetone was added thereto, and a soluble matter was eliminated. Thus, 1.44 g of the acetone-insoluble fraction was obtained.

The obtained insoluble fraction was dissolved in a 50% ethanol aqueous solution to be 1% (w/v) in a concentration to prepare an extract from *Bupleurum rotundifolium*.

Preparation Example 5

Preparation of Seed Extract from *Camellia Sinensis*

A seed extract from *Camellia sinensis* (obtained from Shanghai Youngsun Foods Co., Ltd.) was dissolved in a 50% ethanol aqueous solution to be 1% (w/v) in a concentration to prepare a seed extract from *Camellia sinensis*.

Test Example 1

Permeation Enhancement Test of EGCg Through Small Intestinal Epithelium by Using Epithelial Cell Derived from Human Colon Carcinoma A Caco-2 cell (epithelial cell derived from a human colon carcinoma, obtained from DS Pharma Biomedical Co., Ltd.) was cultured at 37° C. in the presence of 5% $CO_2$. A Caco-2 cell differentiation medium kit (manufactured by Corning Inc.) and BioCoat HTS Fibrillar Collagen Multiwell Insert (24 wells, membrane pore 1 µm, manufactured by Corning Inc.) were used for culture. The Caco-2 cell was suspended in a seeding basal medium to which MITO+™ Serum Extender was added, and seeded on an upper portion of the Insert, and the same medium was also added to a lower portion of the Insert. After the Caco-2 cell was cultured for 24 hours, the above-described seeding basal medium was exchanged for Entero-STIM Enterocyte Differentiation Medium to which the MITO+™ Serum Extender was added. Then, the above-described cell was further cultured for 48 hours, and differentiated into a small intestinal epithelium cell sheet-like form.

In order to confirm formation of tight junction of an intestinal tract, a transepithelial electrical resistance (TEER) value was determined by using Millicell ERS (manufactured by Millipore Corporation) immediately before a permeation enhancement test of EGCg through a small intestinal epithelium, and a Caco-2 cell having a specified value (350 $\Omega \cdot cm^2$) or more was used.

Materials in the upper portion (apical membrane side) and the lower portion (basement membrane side) of the Insert were replaced by HBSS (manufactured by Invitrogen Corporation), and washed twice. Then, EGCg (100 µM, manufactured by Nagara Science Co., Ltd.) and a sample prepared in each of the above-described Preparation Examples were diluted by 1000 times with HBSS (containing 10 mM MES, 5 mM glucose, 10 mM glutamine and 1 mM ascorbic acid, pH 6.0), and added to the upper portion of the Insert. An evaluation concentration of each extract is shown in Table 2. HBSS (containing 10 mM HEPES, 5 mM glucose, 10 mM glutamine and 1 mM ascorbic acid, pH 7.4) was added to the lower portion of the Insert. Then, the Caco-2 cell was cultured for 4 hours.

Then, HBSS in the lower portion of the Insert was collected, and an amount of EGCg permeated through the small intestinal epithelium was quantitatively determined according to the following method.

The amount of EGCg permeated was quantitatively determined by providing the sample for liquid chromatography tandem mass spectrometry (LC-MS/MS). Conditions of the above-described LC-MS/MS are described below.

<LC Conditions>
Column: L-column2 ODS (manufactured by Chemicals Evaluation and Research Institute, Japan)
Mobile phase (ratios are shown in Table 1)
  A) 0.1% aqueous solution of formic acid
  B) Acetonitrile
Flow rate: 0.7 mL/min
Injection volume: 10 µL
<MS Conditions>
MS: 3200 QTRAP
SCAN type: MRM
Polarity: negative
Parameter table: analyte
EGCg; MRM (m/z), 457→169

HBSS (200 μL) collected from the basement membrane side was measured under the above-described LC conditions and the above-described MS conditions, and an amount of EGCg permeated on the basement membrane side was quantitatively determined. Then, a fold change of the amount of EGCg was calculated according to the following formula. The results are shown in Table 2. In Table 2, an amount of EGCg permeated through the Insert when each evaluation sample having the concentration described in Table 2 was added relative to an amount of EGCg permeated through the Insert when each evaluation sample was not added was expressed in terms of (fold change)±(standard error) (N=3 to 4). A significant difference was taken as: P<0.05 (t-test).

(Fold change)=(Permeated EGCg amount when evaluation sample was added)/(Permeated EGCg amount when only EGCg was added)

TABLE 1

| Time (min:sec) | 0:00 | 2:00 | 6:00 | 6:10 | 9:00 | 9:10 | 12:00 |
|---|---|---|---|---|---|---|---|
| A: 0.1% formic acid (volume %) | 97 | 85 | 81 | 10 | 10 | 97 | 97 |
| B: acetonitrile (volume %) | 3 | 15 | 19 | 90 | 90 | 3 | 3 |

Test Example 2

Evaluation of Cytotoxicity by LDH Activity Measurement Test

Cytotoxicity of each evaluation sample was evaluated by collecting HBSS in an upper portion of Insert in Test Example 1, and measuring LDH (Lactate dehydrogenase) activity in a solution according to the following method.

The cytotoxicity was evaluated by using HBSS (100 μL) in the upper portion of the Insert and LDH Cytotoxicity Assay Kit (Cayman Chemical Company). Then, a fold change of LDH activity was calculated according to the following formula. The results are shown in Table 3. In Table 3, a specific activity value of LDH activity when each evaluation sample having the concentration described in Table 3 was added relative to LDH activity when each evaluation sample was not added was expressed in terms of (fold change)±(standard error) (N=3 to 4). A significant difference was taken as: P<0.05 (t-test).

(Fold change)=(LDH activity when evaluation sample was added)/(LDH activity when only EGCg was added)

TABLE 2

Permeability test of EGCg (N = 3-4)

| Evaluation sample | Concentration | Fold change | Significance level |
|---|---|---|---|
| Extract from Kochia scoparia (L.) Schrad. | 0.000% | 1.0 ± 0.1 (Control) | — |
| | 0.0002% | 5.1 ± 0.8 (P = 0.003) | ** |
| | 0.0005% | 50.2 ± 2.1 (P = 0.000) | *** |
| | 0.001% | 76.2 ± 3.2 (P = 0.000) | *** |
| | 0.005% | 90.1 ± 1.4 (P = 0.000) | *** |
| Extract from Acacia concinna | 0.000% | 1.0 ± 0.1 (Control) | — |
| | 0.0002% | 0.8 ± 0.4 (P = 0.544) | — |
| | 0.0005% | 4.2 ± 0.3 (P = 0.000) | *** |
| | 0.001% | 89.2 ± 4.2 (P = 0.000) | *** |
| | 0.005% | 108.4 ± 2.5 (P = 0.000) | *** |
| Extract from Sanicula europaea | 0.000% | 1.0 ± 0.0 (Control) | — |
| | 0.0002% | 1.0 ± 0.1 (P = 0.850) | — |
| | 0.0005% | 5.4 ± 1.6 (P = 0.060) | — |
| | 0.001% | 27.3 ± 0.4 (P = 0.000) | *** |
| | 0.005% | 92.9 ± 1.2 (P = 0.000) | *** |
| Extract from Bupleurum rotundifolium | 0.000% | 1.0 ± 0.1 (Control) | — |
| | 0.001% | 11.5 ± 3.8 (P = 0.032) | * |
| Seed extract from Camellia sinensis | 0.000% | 1.0 ± 0.1 (Control) | — |
| | 0.001% | 2.1 ± 0.1 (P = 0.000) | *** |

\*: P < 0.05 vs control
\*\*: P < 0.01 vs control
\*\*\*: P < 0.001 vs control

As shown in Table 2, Caco-2 cell permeability of EGCg was increased by action of the above-described active ingredient.

The results in Table 2 show that absorption of polyphenol into a living body can be enhanced by administering or ingesting the above-described active ingredient together with polyphenol.

TABLE 3

LDH activity measurement test (N = 3-4)

| Evaluation sample | Concentration | Fold change |
|---|---|---|
| Extract from Kochia scoparia (L.) Schrad. | 0.001% | 1.2 ± 0.1 |
| Extract from Acacia concinna | 0.001% | 1.4 ± 0.1 |
| Extract from Sanicula europaea | 0.001% | 0.7 ± 0.0 |
| Extract from Bupleurum rotundifolium | 0.001% | 1.1 ± 0.0 |
| Seed extract from Camellia sinensis | 0.001% | 0.9 ± 0.1 |

As shown in Table 3, no change was recognized in LDH activity.

The results in Table 3 show that absorption enhancement action of polyphenol into a living body by the above-described active ingredient was not caused by the cytotoxicity.

Test Example 3

Evaluation Test of Blood Migration of Catechins by Using Mice

A test was conducted by using mice (C57BL/6J, male, 7 weeks of age, obtained from CLEA Japan, Inc.) bred under free-feeding of a rodent solid diet (CE-2, manufactured by CLEA Japan, Inc.).

The mice were fasted from food for 16 hours, a body weight of the mice were measured, and a solution dosage was calculated (10 mL/kg body weight). Next, initial blood was collected in an orbital venous plexus under isoflurane anesthesia (heparin-treated micro-hematocrit tube, manufactured by VITREX), and then each catechin solution mentioned later was orally administered into a stomach.

With regard to each catechin solution, three kinds of catechin solutions shown below were prepared by using a catechin preparation (Polyphenon 70S, obtained from Mitsui Norin Co., Ltd.), and the *Kochia scoparia* (L.) Schrad. extract prepared in Preparation Example 1 and the *Acacia concinna* extract prepared in Preparation Example 2.
1. Catechin solution for control group: catechin preparation (100 mg/kg body weight)
2. Catechin solution for low-dose administration group: catechin preparation (100 mg/kg body weight)+*Kochia scoparia* (L.) Schrad. extract or *Acacia concinna* extract (25 mg/kg body weight)
3. Catechin solution for high-dose administration group: catechin preparation (100 mg/kg body weight)+*Kochia scoparia* (L.) Schrad. extract or *Acacia concinna* extract (100 mg/kg body weight)

After 30 minutes, 60 minutes, 90 minutes, 120 minutes and 240 minutes from administration of each solution, blood was collected from the orbital venous plexus under isoflurane anesthesia.

Collected blood was immediately centrifuged at 12,000 rpm for 10 minutes, and 30 µL of plasma was collected into Eppendorf Tubes to which 3 µL of stabilization solution (containing 0.4 M $NaH_2PO_4$ buffer, 20% ascorbic acid and 0.1% EDTA, pH 3.6) was added. The obtained plasma was stored at −80° C. until the measurement mentioned later was performed. The plasma was purified after the deconjugation treatment mentioned later, and concentrations of various catechins in the plasma were measured according to LC-MS/MS.

With regard to the deconjugation treatment, 16 µL of 0.4 M phosphate buffer (pH 3.6), 16 µL of 0.4 M phosphate buffer (pH 7.2), 12 µL of glucuronidase (62.5 U) and 12 µL of sulfatase (0.25 U) were sequentially added to 30 µL of the collected plasma and mixed, and the resultant mixture was incubated at 37° C. for 90 minutes. Next, 600 µL of 0.2 M acetic acid solution and 100 µL of internal standard (ethyl gallate, 10 ng/mL) solution were added thereto and mixed.

A solid-phase column (Oasis HLB Cartridge 10 mg, 1 cc) was used for extraction and purification of catechins. The solid-phase column was sequentially conditioned with 1 mL of distilled water, 1 mL of DMSO (containing 0.1% acetic acid) and 1 mL of distilled water, and a solution after the deconjugation treatment was passed through the column. Next, as cleaning operation of the column, 2 mL of distilled water and 1 mL of 30% methanol were passed therethrough, and the catechins were eluted by 1 mL of DMSO (containing 0.1% acetic acid and 0.05% ascorbic acid) to collect the resultant material into a 15 mL centrifuging tube. The resultant material was freeze-dried, dissolved in 1 mL of methanol (containing 0.05% ascorbic acid), concentrated by centrifugation under reduced pressure, and finally dissolved in 30 µL of 10% acetonitrile (containing 0.5% ascorbic acid) solution.

A concentrated sample was introduced into LC-MS/MS, and an amount of each catechin was quantitatively determined from a peak area. LC conditions were set in the same manner as in Test Example 1. MS conditions were adjusted as described below.
<MS Conditions>
MS: 3200 QTRAP
SCAN type: MRM
Polarity: negative
Parameter table: analyte,
EGCg; MRM (m/z), 457→169
ECg; MRM (m/z), 441→289

Figure 1:
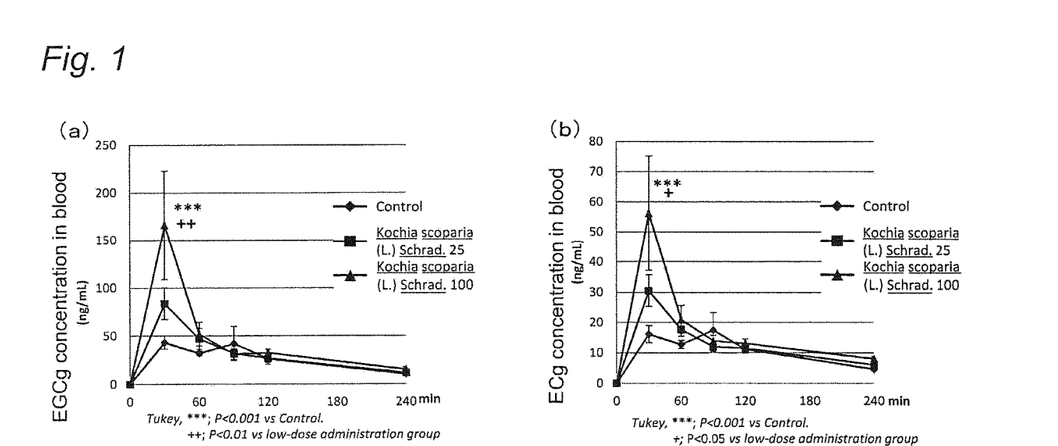
FIG. 1(a) is a graph showing a change over time of an epigallocatechin gallate concentration in blood when a *Kochia scoparia* (L.) Schrad. extract is orally administered into a stomach of mice, which are performed in Test Example 3.
FIG. 1(b) is a graph showing a change over time of an epicatechin gallate concentration in blood when a *Kochia scoparia* (L.) Schrad. extract is orally administered into a stomach of mice, which are performed in Test Example 3.
Figure 2:
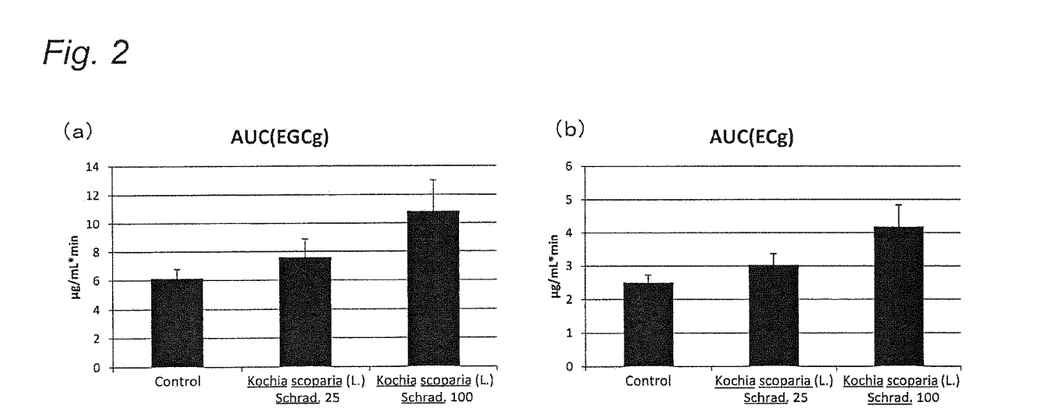
FIG. 2(a) is a graph showing an area under an epigallocatechin gallate concentration in blood-time curve (AUC) of the graph shown in FIG. 1(a).
FIG. 2(b) is a graph showing an area under an epicatechin gallate concentration in blood-time curve (AUC) of the graph shown in FIG. 1(b).
Figure 3:
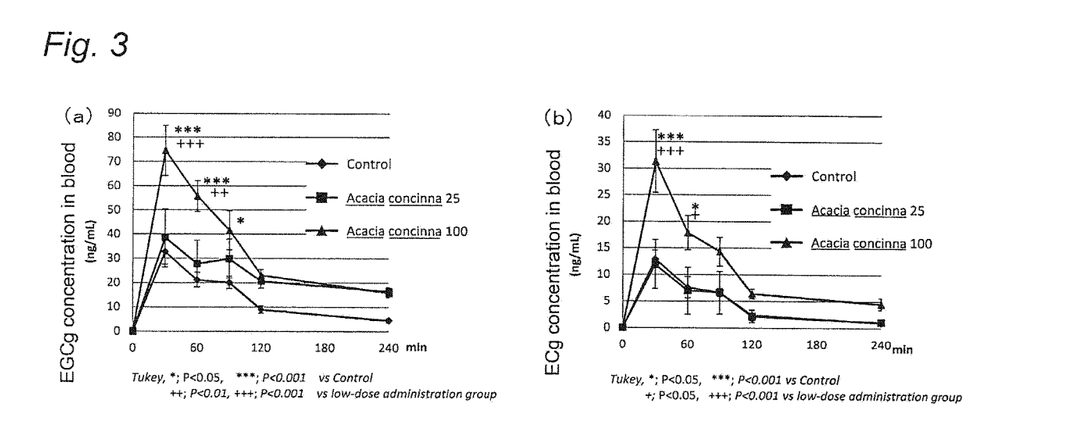
FIG. 3(a) is a graph showing a change over time of an epigallocatechin gallate concentration in blood when an *Acacia concinna* extract is orally administered into a stomach of mice, which are performed in Test Example 3.
FIG. 3(b) is a graph showing a change over time of an epicatechin gallate concentration in blood when an *Acacia concinna* extract is orally administered into a stomach of mice, which are performed in Test Example 3.
Figure 4:
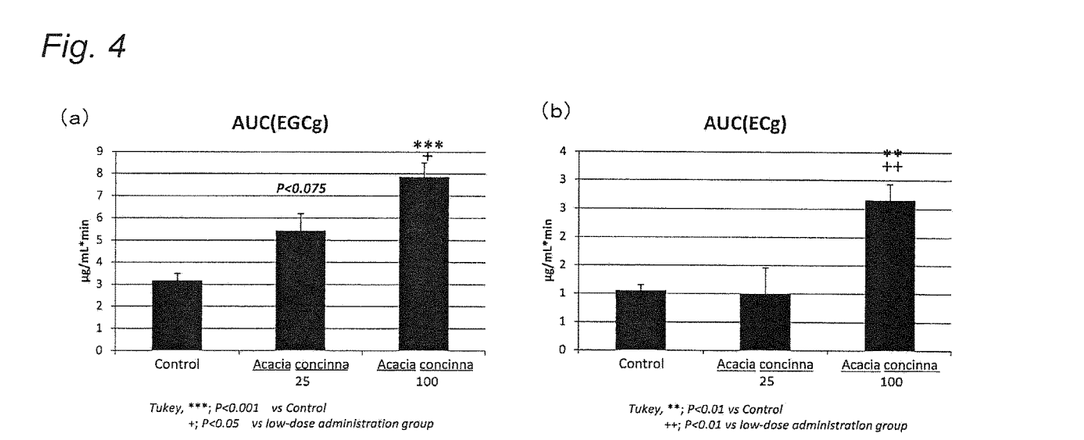
FIG. 4(a) is a graph showing an area under an epigallocatechin gallate concentration in blood-time curve (AUC) of the graph shown in FIG. 3(a).
FIG. 4(b) is a graph showing an area under an epicatechin gallate concentration in blood-time curve (AUC) of the graph shown in FIG. 3(b).

A change over time of the catechin (EGCg and ECg) concentration in blood when the *Kochia scoparia* (L.) Schrad. extract was orally administered into the stomach of the mice are shown in FIG. 1. Moreover, AUC in each graph shown in FIG. 1 is shown in FIG. 2. Furthermore, a change over time of the catechin (EGCg and ECg) concentration in blood when the *Acacia concinna* extract was orally administered into the stomach of the mice are shown in FIG. 3. Moreover, AUC in each graph shown in FIG. 3 is shown in FIG. 4.

In addition, in FIG. 1 and FIG. 2, the term "*Kochia scoparia* (L.) Schrad. 25" means a *Kochia scoparia* (L.) Schrad. extract low-dose administration group, and the term "*Kochia scoparia* (L.) Schrad. 100" means a *Kochia scoparia* (L.) Schrad. extract high-dose administration group. Further, in FIG. 3 and FIG. 4, the term "*Acacia concinna* 25" means an *Acacia concinna* extract low-dose administration group, and the term "*Acacia concinna* 100" means an *Acacia concinna* extract high-dose administration group.

All of the results obtained were expressed in terms of (average±standard error) (N=4 to 8). In a significance test, Two-way ANOVA Tukey was used for the change over time (FIG. 1 and FIG. 3) of the catechin concentration in blood, One-way ANOVA Tukey was used for AUC (FIG. 2 and FIG. 4), and a level: $P<0.05$ was applied as a significance level. In addition, an individual exhibiting an outlier in AUC was rejected at a level of significance of 5% according to the Smirnov-Grubbs test.

When the *Kochia scoparia* (L.) Schrad. extract was administered, a maximum EGCg concentration in blood (after 30 minutes from administration of the *Kochia scoparia* (L.) Schrad. extract) was increased to 1.94 times in the low-dose administration group and 3.84 times in the high-dose administration group, respectively, in comparison with the control group (see FIG. 1(*a*)). Moreover, a similar trend was recognized also in ECg, and a maximum ECg concentration in blood (after 30 minutes from administration of the *Kochia scoparia* (L.) Schrad. extract) was increased to 1.89 times in the low-dose administration group and 3.48 times in the high-dose administration group, respectively (see FIG. 1(*b*)).

Further, as shown in FIG. 2, an upward trend was recognized in $AUC_{0-240\ min}$ of EGCg and ECg when the *Kochia scoparia* (L.) Schrad. extract was administered. Specifically, $AUC_{0-240\ min}$ of EGCg and $AUC_{0-240\ min}$ of ECg were increased to 1.73 times and 1.61 times in the *Kochia scoparia* (L.) Schrad. extract high-dose administration group, respectively, in comparison with the control group (see FIGS. 2(*a*) and 2(*b*)).

As shown in the results described above, the *Kochia scoparia* (L.) Schrad. extract is considered to have action of increasing blood migration of catechins such as EGCg and ECg.

When the *Acacia concinna* extract was administered, a maximum EGCg concentration in blood (after 30 minutes from administration of the *Acacia concinna* extract) was increased to 2.28 times in the high-dose administration group, in comparison with the control group (see FIG. 3(*a*)). Moreover, a maximum ECg concentration in blood (after 30 minutes from administration of the *Acacia concinna* extract) was increased to 2.43 times in the high-dose administration group, in comparison with the control group (see FIG. 3(*b*)).

Further, as shown in FIG. 4, a statistically significant increasing was recognized in $AUC_{0-240\ min}$ of EGCg and ECg in the high-dose administration group when the *Acacia concinna* extract was administered. Specifically, $AUC_{0-240\ min}$ of EGCg and $AUC_{0-240\ min}$ of ECg were increased to 2.49 times and 2.53 times in the *Acacia concinna* extract high-dose administration group, respectively, in comparison with the control group (see FIGS. 4(*a*) and 4(*b*)).

As shown in the results described above, the *Acacia concinna* extract is also considered to have action of increasing blood migration of catechins such as EGCg and ECg.

Test Example 4

Permeation Enhancement Test of Chlorogenic Acid Through Small Intestinal Epithelium by Using Epithelial Cell Derived from Human Colon Carcinoma A permeation test of chlorogenic acid (100 μM, manufactured by Sigma-Aldrich) through a small intestinal epithelium was conducted by using the sample prepared in each of the above-described Preparation Examples, according to the method of the permeation test of EGCg in Test Example 1. Then, HBSS in a lower portion of Insert was collected, and an amount of chlorogenic acid permeated through the small intestinal epithelium was quantitatively determined according to the method of quantitatively determining the amount of EGCg in Test Example 1.
<LC Conditions>
Column: L-column2 ODS (manufactured by Chemicals Evaluation and Research Institute, Japan)
Mobile phase (ratios are shown in Table 4)
  A) 0.1% aqueous solution of formic acid
  B) Acetonitrile
Flow rate: 0.7 mL/min
Injection volume: 10 μL
<MS Conditions>
MS: 4500 QTRAP
SCAN type: MRM
Polarity: negative
Parameter table: analyte
Chlorogenic acid; MRM (m/z), 353.0→191.1

TABLE 4

| Time (min:sec) | 0:00 | 0:48 | 4:00 | 5:00 | 5:06 | 6:00 |
|---|---|---|---|---|---|---|
| A: 0.1% formic acid (volume %) | 98 | 98 | 5 | 5 | 98 | 98 |
| B: acetonitrile (volume %) | 2 | 2 | 95 | 95 | 2 | 2 |

A concentration of chlorogenic acid permeated therethrough is shown in Table 5. In Table 5, the concentration is expressed in terms of (chlorogenic acid concentration permeated through Insert when each sample was added)± (standard error). A significant difference was taken as: $P<0.05$ (t-test).

TABLE 5

Permeability test of chlorogenic acid (N = 3-4)

| Evaluation sample | Permeated concentration (μM) | Significance level |
|---|---|---|
| Control (chlorogenic acid 100 μM) | 0.015 ± 0.007 | — |
| +Extract from *Kochia scoparia* (L.) Schrad. (0.001%) | 0.198 ± 0.005 | *** |
| +Extract from *Acacia concinna* (0.001%) | 0.412 ± 0.014 | *** |
| +Extract from *Sanicula europaea* (0.001%) | 0.297 ± 0.014 | *** |
| +Extract from *Bupleurum rotundifolium* (0.001%) | 0.206 ± 0.012 | *** |
| +Seed extract from *Camellia sinensis* (0.001%) | 0.225 ± 0.011 | *** |

***: $P < 0.001$ vs Control (chlorogenic acid 100 μM)

As shown in Table 5, Caco-2 cell permeability of chlorogenic acid was increased by action of the above-described active ingredient.

The results in Table 5 show that absorption of chlorogenic acid into a living body can be enhanced by administering or ingesting the above-described active ingredient together with chlorogenic acid.

As described above, the plant extracts specified according to the present invention each have action of enhancing the absorption of polyphenol including tea catechins such as EGCg and ECg and a chlorogenic acid compound such as chlorogenic acid into the living body.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2015-244659 filed in Japan on Dec. 15, 2015, which is entirely herein incorporated by reference.

What is claimed is:

1. A method of enhancing absorption of a polyphenol, comprising administering to a human or non-human animal or ingesting a composition comprising a therapeutically effective amount of at least one plant extract selected from the group consisting of an extract from *Kochia scoparia* (L) Schrad., an extract from *Acacia concinna*, an extract from *Sanicula europaea*, an extract from *Bupleurum rotundifolium*, and a seed extract from *Camellia sinensis*.

2. The method according to claim 1, wherein the plant extract enhances absorption of the polyphenol from the intestinal tract into the circulatory system.

3. The method according to claim 1, wherein the plant extract is administered to a person who desires an antiaging effect, a life-extension effect, a cognitive function maintaining effect, an antioxidative effect, a sterilizing effect, a treatment effect on an infectious disease, a relieving effect of an infectious disease symptom, an anticancer effect, an antitumor effect, a hypotensive effect, a blood sugar level elevation inhibitory effect, a body fat-reducing effect, an anti-fatigue effect or improvement of stamina, a treatment of diabetes mellitus or insulin resistance, and/or a treatment of high postprandial blood sugar.

4. The method according to claim 1, wherein the amount of the plant extract administered or ingested is between 0.001 mg/kg body weight/day and 50 mg/kg body weight/day.

5. The method according to claim 1, wherein the composition further comprises one or more polyphenols, or wherein the composition is a food or drink comprising the plant extract, or wherein the composition is a food or drink comprising the plant extract and one or more polyphenols.

6. The method according to claim 5, wherein the amount of the active ingredient in the plant extract in the composition is between 0.01 parts by mass and 500 parts by mass, relative to 100 parts by mass of the one or more polyphenols.

7. The method according to claim 5, wherein, if the composition does not comprise one or more polyphenols, a second composition comprising one or more polyphenols is administered or ingested, wherein the compositions are administered or ingested simultaneously or so that they reach the intestinal tract substantially simultaneously.

8. The method according to claim 1, wherein the polyphenol is selected from the group consisting of epigallocatechin, epicatechin, catechin, gallocatechin, epigallocatechin gallate, epicatechin gallate, catechin gallate, and gallocatechin gallate.

9. The method according to claim 1, wherein the polyphenol is selected from the group consisting of caffeoylquinic acid, feruloylqunic acid, and dicaffeoylquinic acid.

10. The method according to claim 1, wherein the extract from *Kochia scoparia* (L.) Schrad. is an extract of the fruit of the *Kochia scoparia* (L.) Schrad.

11. The method according to claim 1, wherein the extract from *Acacia concinna* is an extract of the root of the *Acacia concinna*.

12. The method according to claim 1, wherein the extract from *Sanicula europaea* is an extract of the leaf of the *Sanicula europaea*.

13. The method according to claim 1, wherein the extract from *Bupleurum rotundifolium* is an extract of the root of the *Bupleurum rotundifolium*.

* * * * *